United States Patent [19]

Kell et al.

[11] Patent Number: 4,810,650
[45] Date of Patent: Mar. 7, 1989

[54] DETERMINATION OF BIOMASS

[76] Inventors: Douglas B. Kell, Cwmdarren, Penbont-Rhydybeddau, Cwmsymlog, SY23 3HR, Wales; Robert W. Todd, Bryncaemeilir, SY20 80G, Wales

[21] Appl. No.: 99,594

[22] Filed: Sep. 22, 1987

[30] Foreign Application Priority Data

Sep. 22, 1986 [GB] United Kingdom ............... 8622748

[51] Int. Cl.⁴ .................. C12M 1/; C12M 34; G01R 11/52
[52] U.S. Cl. .................. 435/291; 435/286; 435/284; 324/60 R; 324/60 C
[58] Field of Search ............ 435/286, 284, 291; 324/60 R, 60 C, 61 R

[56] References Cited

U.S. PATENT DOCUMENTS

| | | | |
|---|---|---|---|
| 3,338,412 | 9/1967 | Maltby | 324/61 R |
| 3,765,841 | 10/1973 | Paulson et al. | 435/291 X |
| 3,930,957 | 1/1976 | Cummings et al. | 435/289 X |
| 3,984,766 | 10/1976 | Thornton | . |
| 4,156,180 | 5/1979 | Annen et al. | 435/291 |
| 4,214,203 | 7/1980 | Coster et al. | . |
| 4,246,534 | 1/1981 | Jacobi et al. | 324/61 R |
| 4,250,266 | 2/1981 | Wade | 435/289 |
| 4,288,741 | 9/1981 | Dechene et al. | 324/61 R |
| 4,318,992 | 3/1982 | Mila-de-la-Roca et al. | 435/291 |
| 4,547,735 | 10/1985 | Kiesewetter et al. | . |
| 4,564,444 | 1/1986 | Hiraoka et al. | 435/291 |

FOREIGN PATENT DOCUMENTS

| | | |
|---|---|---|
| 0061544 | 3/1981 | European Pat. Off. . |
| 0101880 | 7/1983 | European Pat. Off. . |
| 2412166 | 9/1975 | Fed. Rep. of Germany . |
| 1561431 | 2/1980 | United Kingdom . |
| 2029026 | 3/1980 | United Kingdom . |
| 2131954 | 6/1984 | United Kingdom . |

OTHER PUBLICATIONS

Hause, L. L., "Electrode and Electrolyte Impedance in the Detection of Bacterial Growth", IEEE Transactions on Biomedical Engineering, vol. BME-28, No. 5, May 1981.
Meyer, H. P., et al., "Growth Control in Microbial Cultures",: Ann. Rev. Microbial. 1985, pp. 299–309.
Harris, C. M., et al., "Dielectric Permittivity of Microbial Suspensions at Radio Frequencies: A Novel Method for the Real-Time Estimation of Microbial Biomass," Enzyme Microb. Technol., 1987, vol. 9, Mar.
Pirt, "Principles of Microbe and Cell Cultivation," Blackwell, 1975, pp. 14–21.
Carleysmith, S. W., et al., "Fermenter Instrumentation and Control," Advances in Biotechnological Processes 3, 1984, pp. 22–23.
Harris, C. M., et al., "The Estimation of Microbial Biomass," Biosensors 1 (1985), pp. 17–84.

*Primary Examiner*—Larry Jones
*Attorney, Agent, or Firm*—Cushman, Darby & Cushman

[57] ABSTRACT

Apparatus for the determination of biomass in a suspension and its use in a fermentation apparatus. The apparatus includes electrodes to be placed in the suspension and the following other components: circuit for applying an alternating voltage between the electrodes; circuit for providing a current signal indicative of the current in the current electrode circuit; circuit for providing a voltage signal indicative of the voltage between the ratio between the value of the voltage signal and the value of a quadrature component of the current signal, or vice versa, to provide a capacitance dependent signal.

12 Claims, 3 Drawing Sheets

DETERMINATION OF BIOMASS

BACKGROUND OF THE INVENTION

1. Field of the Art

This invention relates to apparatus for the determination of biomass in a culture and to a fermentation process in which the apparatus is used as a control feature. This application is related to U.S. application Ser. No. 099,595 filed Sept. 22, 1987.

2. Description of the Prior Art

There is increasing interest in biotechnology, both in the traditional fermentation industry and in the exploitation of living cells in new processes to produce commercially useful products such as antibiotics, vitamins, amino acids and a variety of biologically active proteins.

The productivity of fermentation processes is dependent to a considerable extent upon culture conditions. It is therefore desirable, and has now become conventional, to control those variables such as pH and dissolved oxygen tension for which sensors are available.

One of the most important variables in a fermention process is the reactor biomass concentration, i.e. the concentration of microbial or other cells in the fermenter, since the productivity under a given set of process conditions is directly proportional to this. However, to date no accurate means has been developed for measuring the biomass content of a culture in real time, i.e. for measuring the present biomass content rather than the biomass content some time in the past.

The lack of suitable means to measure this important process variable has been commented upon by several writers in recent years, see for example: Pirt, "Principles of Microbe and Cell Cultivation", Blackwell, 1975, p 16; Carleysmith and Fox, "Fermenter Instrumentation and Control," Adv. Biotechnol. Processes 3, 1–51, 1984; and Harris and Kell, "The estimation of Microbial Biomass," Biosensors J.1, 17–84 (1985).

This last reference notes (1) that the most appropriate measure suitable for estimating biomass in real time is the biovolume, i.e. the volume fraction of a culture enclosed by the cytoplasmic membranes of the microbial or other cells within it, (2) that the only means by which biomass might be estimated in real time will be by physical as opposed to chemical measurements, and (3) that all presently available physical methods such as light scattering) for estimating biomass, are essentially unusable under the difficuclt conditions existing in a fermenter.

SUMMARY OF THE INVENTION

It is an object of the present invention to provide a measurement of the microbial or other biomass in fermenters in real time and preferably in situ.

In our co-pending UK patent application No. 8622747 we claim a method for the determination of biomass in a medium comprising a suspending fluid particularly a liquid and cells, the method comprising generating a signal dependent on the electrical capacitance, at a suitable frequency, between electrodes mutally spaced in the medium, and determining from the capacitance dependent signal, the volume fraction of the medium enclosed by the cytoplasmic membranes of the cells (biovolume).

Further in our co-pending UK patent application No. 8622747 we also claim a fermentation process utilising a culture comprising a suspending liquid and cells, the method comprising generating a signal dependent on the electrical capacitance, at a predetermined frequency, between electrodes mutally spaced in the culture or a sample thereof, and providing an indication if the capacitance dependent signal differs from a predetermined value or falls outside a predetermined range, and/or altering the value of a process parameter to return the signal towards the predetermined value or the predetermined range, said predetermined frequency being such that the capacitance between the electrodes depends on the volume fraction of the culture enclosed by the cytoplasmic membranes of the cells.

Yet further in our UK patent application No. 8622747 we claim apparatus for performing a fermentation process utilising a culture comprising a suspending liquid and cells, the apparatus comprising: a fermenter for containing the culture, electrodes mutally spaced in the fermenter so as to be in contact with the culture in use; and means for generating a signal dependent on the capacitance between the electrodes, at a predetermined frequency.

The method of the invention may be used to determine biomass in any medium. The method is most useful for determining biomass in a culture and will generally be described in relation to such use in this specification. However it may also be used to determine biomass suspended in aqueous and in other suspensions and for instance in emulsions.

The apparatus may include means to determine whether the capacitance dependent signal differs from a predetermined value or falls outside a predetermined range of values.

The apparatus may further include means responsive to the means to determine, for altering one or more parameters of the process to return the capacitance dependent signal towards the predetermined value or the predetermined range.

There is an important relationship between the apparent relative permittivity of a suspension of spherical cells measured at a particular frequency, the cell radius, and the cell volume. The relationship can be expressed by the equation:

$$L = \frac{9PrC_m}{4r} +$$

where

L is the apparent relative permittivity of the culture

P is the volume fraction of the culture occupied by cells r is the cell radius $C_m$ is the capacitance of the cell membrane per unit area, and is the permittivity of the culture at a frequency which is high with respect to the measuring frequency r is the permittivity of free space, approximately $8.85 \times 10^{-12}$ F/m.

For non-spherical cells, the factor 9/4 is modified.

Permittivity is related to capacitance, which can be measured, by a factor, referred to as the cell constant, which depends on the electrode number, size and geometry. The permittivity of a sample can thus be determined by measuring the capacitance between electrodes mutually spaeed therein. Formerly permittivity was known as dielectric constant.

The relative permittivity of an aqueous solution is dimensionless and depends slightly on the temperature and electrical conductivity of the sample but is always in the range 60 to 85, very often being approximately 78. The permittivity of aqueous solutions, when measured at low voltages, is independent of frequency up to approximately 1 GHz, and under the conditions normally pertaining in a fermenter, is essentially unaffected by the presence of dissolved gases and non-cellular particulate matter.

The permittivity of an aqueous solution forms a reference or baseline against which the cell content of a culture may be determined.

The permittivity of a cellular suspension is strongly dependent upon frequency. For example, the permittivity at 100 kHz, of a suspension of bacterial cells of radius 0.5 $\mu$m and occupying a volume fraction of 0.1, might be approximately 250. This value will decrease towards a baseline value corresponding essentially to that of the suspending liquid as the frequency is increased.

The frequency dependent increase in permittivity found for cell suspensions over the baseline value for an aqueous solution, is known as a dispersion. Three major dispersions ($\alpha$ $\beta$, and $\gamma$ dispersions) are generally recognised, with the $\beta$-dispersion being particularly important for the invention. The $\alpha$-dispersion occurs at lower frequencies than the $\beta$-dispersion and is mainly caused by the presence of mobile ions at the cell surface. The $\gamma$-dispersion occurs at higher frequencies than the $\beta$-dispersion and is caused predominantly by the rotation of dipolar species such as water. The $\alpha$-dispersion is highly dependent on the structure of the cell wall, whilst the $\gamma$-dispersion is not specific for intact cells.

The $\beta$-disperion of the dielectric permittivity was named by H P Schwan (Advances in Biological and Medical Physics, Vol. 5, 147–209, 1957). It is caused mainly by the presence of relatively ion-impermiable cellular membranes and has the approximate shape of an inverted sigmoid. Its magnitude for spherical cells, given $C_m$, can be taken to be dependent only upon cell radius and the volume fraction occupied by the cells. Other influences are, or can be taken to be, constants. Its position on the frequency axis depends upon the cell radius and the internal and external electrical conductivities. The large magnitude of the $\beta$-dispersion is due to cells having a conducting interior separated from the exterior by a poorly-conducting membrane providing a large capacitance, for example 1 $\mu$F/cm$^2$. Its magnitude is therefore directly proportional to the volume fraction occupied by the cells. The magnitude of the $\beta$-dispersion is large relative to the effects of non-cellular particles, dissolved gasses or oil droplets in the suspension. This allows the biovolume (related to the biomass by the density of the cell cytoplasm) to be measured without being significantly affected by particles or oil droplets in cell suspensions. The $\beta$-dispersion is a property of intact cells (see Pethig "Dielectric and Electronic Properties of Biological materials", Wiley, 1979) and its magnitude is directly proportional to the volume fraction of cells in a suspension up to very high volume fractions.

Suitable frequencies for measurement of biomass include frequencies at which the $\beta$-dispersion is substantially complete but at which the $\alpha$-dispersion is substantially insignificant. Measurements of the whole of the $\beta$-dispersion may be made, but optimum measuring frequencies are in the half of the $\beta$-dispersion which occurs at lower frequencies before the $\alpha$-dispersion is reached. Suitable frequencies include radio frequencies from 0.1 to 10 MHz, especially 0.1 MHz to 1 MHz, with a preferred range being 0.2 to 0.3 MHz. For large cells frequencies below 0.1 MHz may be found suitable, whilst for cultures having a high electrical conductivity, frequencies in excess of 1 MHz may be found suitable.

The method of the invention can be used to determine the biomass content of a wide range of cultures, including plant, animal and microbial cell cultures, and the fermentation process can be used to produce a wide variety of products. Most usefully, however, the method of the invention is applicable to microbial cultures containing bacterial, yeast or fungal cells. Frequently the suspending liquid will be an aqueous culture medium containing nutrients suitable for the cells suspended in it, for example compounds containing carbon, phosphorus, nitrogen and other sources of essential nutrients.

The fermentation process of the invention can be carried out in any type of fermenter. Permittivity can be determined by measuring the capacitance between electrodes mutually spaced in a sample of the culture. This can be done using a bridge or other circuit. Preferably the measuring electrodes are attached to the fermenter used in the process of the invention to enable direct on-line measurements to be made. Alternatively, samples may be withdrawn from the fermenter.

BRIEF DESCRIPTION OF THE DRAWINGS

Examples of the method and process, and an embodiment of the apparatus of the invention, will now be described with reference to the accompanying drawings, in which.

DETAILED DESCRIPTION OF THE PREFERRED EMBODIMENT

Figure 4:
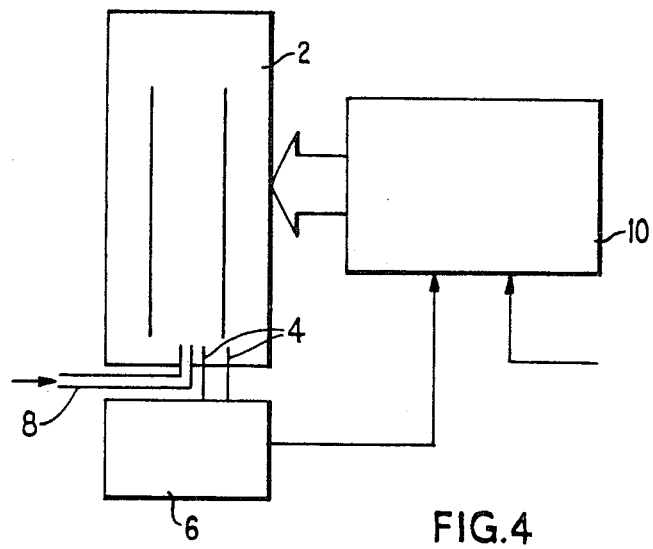
FIG. 4 is a schematic diagram of apparatus embodying the invention.

Referring to FIG. 4, a gas-lift fermenter 2 has a pair of spaced wire electrodes 4 fitted in the base. The electrodes 4 are connected to respective terminals of a Hewlett Packard low frequency impedance analyser 6 type No. 4192A. In order to reduce the effects of the capacitance inherent in the connecting leads, the impedance analyser 6 is placed as close as possible to the connections with the electrodes. Indeed, the impedance analyser may be beneath the fermenter. In order to reduce the effects of polarisation of the culture medium at the electrodes, these are platinum black. Air is supplied to the culture via an inlet 8.

Figure 1:
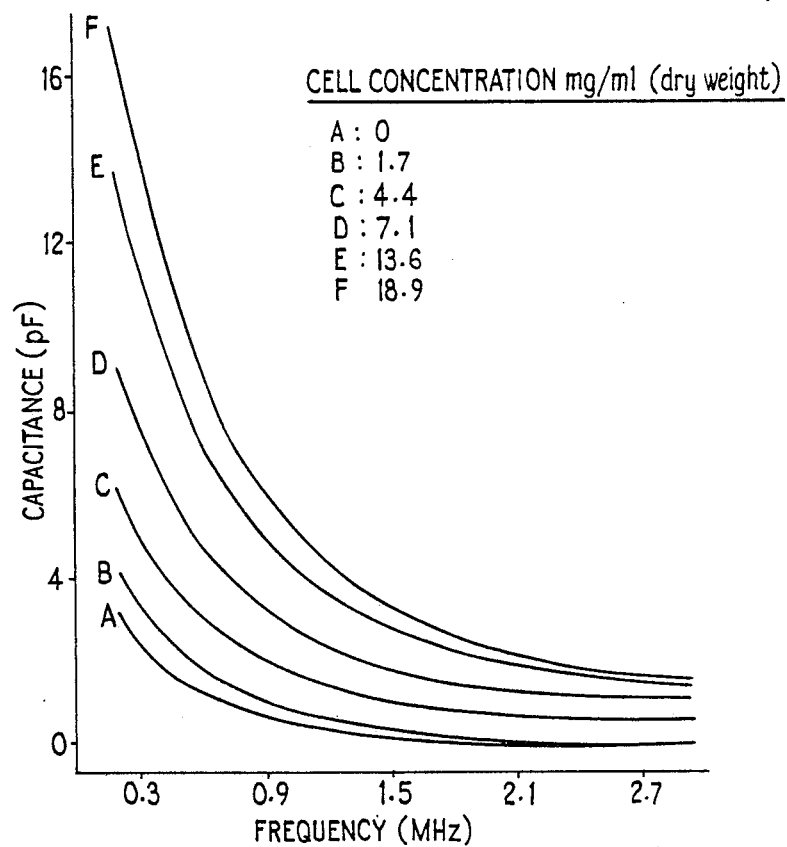
FIG. 1 shows typical variations of capacitance against frequency at different concentrations of cells in a culture.
Figure 2:
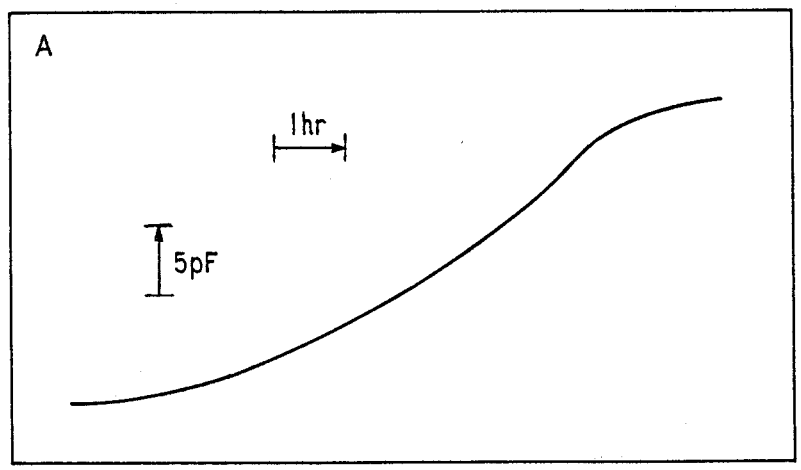
FIG. 2 shows the variation with time of capacitance, at fixed frequency, as a culture grows in a gas-lift fermenter.
Figure 3:
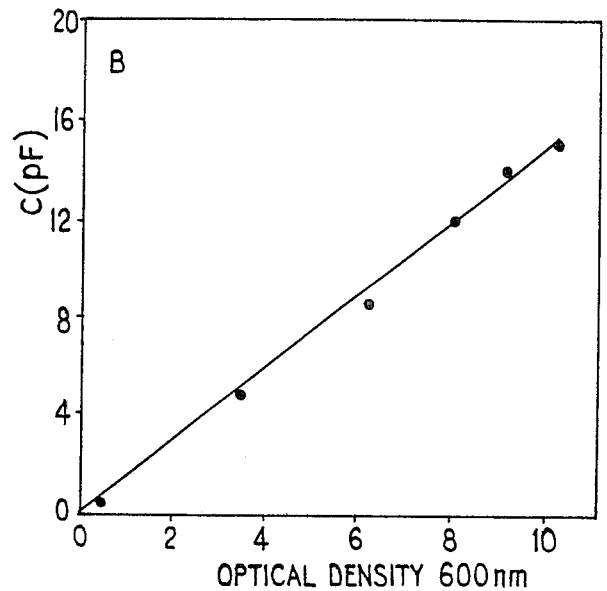
FIG. 3 shows the capacitance plotted against optical density of samples withdrawn from the fermenter.

*Saccharomyces cerevisiae* is grown in the gas-lift fermenter. The culture medium contains 5% (w/v) malt extract and 0.5% (w/v) yeast extract. The initial pH is adjusted to 4.5 and the temperature is 30 degrees centigrade. The conductance of this medium is ca. 1.57 mS/cm. Typical frequency dependent capacitance is shown in FIG. 1 at a number of different cell concentrations. It is evident that there is a sizable dielectric dispersion which depends on cell concentration. The dispersion corresponds in magnitude and relaxation time to the β-dispersion. At a fixed frequency of 0.3 MHz, FIGS. 2 and 3 show respectively, the change in capacitance with time and against the optical density of samples taken from the fermenter and appropriately diluted.

The productivity of a fermentation process is dependent on culture conditions. One of the important variables in the fermentation process which it is advantageous to measure, is the biomass concentration. It may also be advantageous to run the fermentation at a particular biomass concentration, or with the concentration within a predetermined range.

The apparatus described above can be calibrated to determine the capacitance at a fixed frequency, say 0.3 MHz, corresponding to particular biomass concentrations. The apparatus may be calibrated to indicate biomass directly.

The on line measurement of capacitance, or biomass, provides a capacitance dependent signal which is fed to a process controller 10 where it is compared with a reference signal. Alternatively the process controller 20 may determine whether the capacitance dependent signal lies within a predetermined range. The process controller is arranged to adjust one or more parameters of the fermentation process to return the capacitance dependent signal towards the reference signal value or towards the predetermined range. Parameters which may be adjusted include the oxygen rate, i.e. the air supply rate, the dilution rate, the rate of addition of nutrients or new culture in a continuous process, the temperature, and so on.

According to the present invention we provide apparatus for determining biomass in a medium comprising a suspending fluid and cells, the apparatus comprising: mutually spaced electrodes for placing in the medium in electrical contact therewith; and means for generating a signal dependent on the capacitance between the electrodes, at a predetermined frequency or over a predetermined range of frequencies between 0.1 MHz and 10 MHz, especially 0.1 MHz and 1.0 MHz said electrodes including a pair of voltage sensing electrodes between a pair of current electrodes, and the means for generating the capacitance dependent signal, comprising: means for applying an alternating voltage, at the predetermined frequency, between the current electrodes; means for providing a current signal indicative of the instantaneous current in the current electrode circuit; means for providing a voltage signal indicative of the instantaneous voltage between the voltage electrodes; and means for determining the ratio between the value of the voltage signal and the value of a quadrature component of the current signal, or vice versa, to provide the capacitance dependent signal.

Further according to the present invention we provide apparatus for performing a fermentation utilising a culture comprising a suspending liquid and cells, the apparatus comprising: a fermenter for containing the culture, electrodes mutually spaced in the fermenter so as to be in contact with the culture in use including a pair of voltage sensing electrodes between a pair of current electrodes and means for generating a signal dependent on the capacitance between the electrodes, at a predetermined frequency, and wherein the means for generating the capacitance dependent signal, comprises: means for applying an alternating voltage, at the predetermined frequency, between the current electrodes; means for providing a current signal indicative of the instantaneous current in the current electrode circuit; means for providing a voltage signal indicative of the instantaneous voltage between the voltage electrodes; and means for determing the ratio between the value of the voltage signal and the value of a quadrature component of the current signal, or vice versa, to provide the capacitance dependent signal.

Whereas it is quite possible to generate the capacitance dependent signal, using the apparatus described above, the Hewlett Packard low frequency impedance analyser is not ideally suited to the conditions imposed by an industrial fermenter. For example there is the need to place the analyser close to the fermenter as mentioned above. It would also be useful to have a system to accommodate any polarisation which does occur at the electrodes, rather than relying entirely on the use of platinum black to reduce it. Further, the Hewlett Packard analyser was not found particularly suited to measuring the capacitance in the presence of a low common mode impedance to earth, which could well exist in an industrial fermenter.

Figure 5:
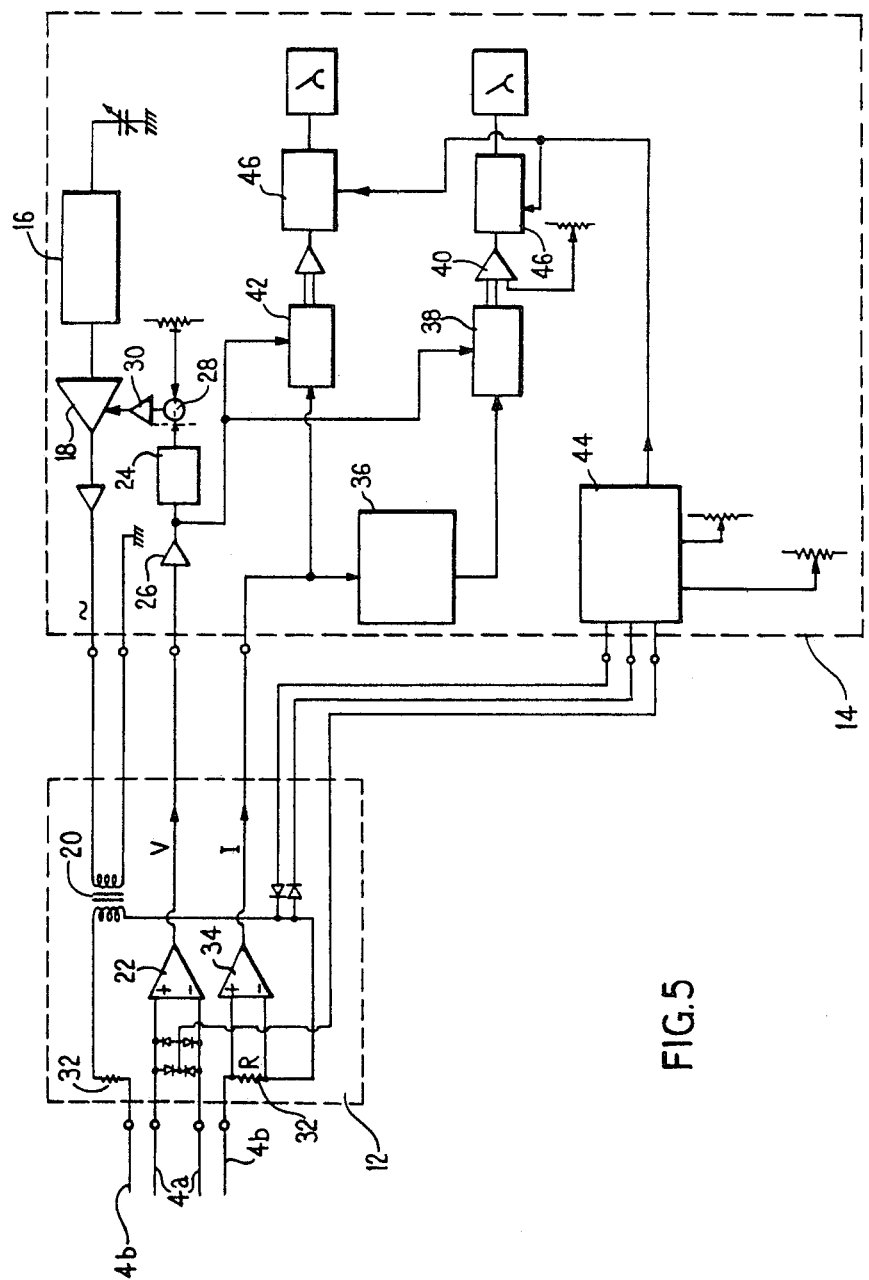
FIG. 5 is a circuit diagram of a modified apparatus embodying the present invention.

The circuit illustrated in FIG. 5 is intended to address these problems.

In order to deal with the potential problem of polarization, two pairs of (cheaper) stainless steel electrodes are used. The electrodes, still in the form of wires, are arranged parallel, as illustrated, and in a linear array so that two of the electrodes 4a are between the others 4b. The outer current electrodes 4b are used to pass current through the culture, and it is at these electrodes that any polarization will occur, if at all. The inner electrodes are used to sense the voltage across the gap between them. The apparatus uses the current passed between the current electrodes and the voltage sensed by the voltage sensing electrodes, to generate a signal dependent on the capacitance between the voltage sensing electrodes. The capacitance dependent signal has a different magnitude from that which would be obtained without the separate current electrodes (in the complete absence of polarization), since less of the current passes through the space between the voltage sensing electrodes. However, the signal obtained is still a good measure of the capacitance.

To reduce the effects of the impedance of the connections to the electrodes, part of the circuit is contained in a probe unit 12 connected directly to the electrodes. The remainder of the circuit is contained in a main unit 14 which may be located remote from the ferementer.

A variable frequency oscillator, preferably operable in the range 0.1 to 10 MHz supplies a current to the current electrodes 4b, via a voltage controlled variable gain amplifier 18 and an isolating transformer 20 which avoids undesirable ground loop currents.

The voltage sensing electrodes 4a are each connected to a respective input of a wide band amplifier 22 which has a high input impedance and good common mode rejection. The amplifier 22 is contained in the probe unit 12, so that its connections to the electrodes 4a are as short as possible.

The output signal of the amplifier 22 is representative of the instantaneous voltage between the electrodes 4a, and is fed to the input of a detector 24 via another amplifier 26, both in the main unit. The output of the detector 24, is a signal representative of the amplitude of the voltage between the voltage sensing electrodes 4a. This is subtracted from a voltage reference level in a circuit 28, the output of which is fed to the control input of the voltage controlled amplifier 18 via a further amplifier 30 to complete a negative feedback control loop.

The control loop maintains the voltage between the voltage sensing electrodes constant and independent of any polarization which might occur at the current electrodes 4b. As there is essentially no current flow in the external circuit between the voltage sensing electrodes, they are free from the effects of polarization, with the result that the ratio of the voltage between the electrodes 4a and the current between the electrodes 4b is an impedance term representative of the impedance of the bulk matter between the electrodes 4a. For the measurement of biomass, the capacitive part of the impedance is of particular interest.

A pair of resistors 32 is included in series with the current electrodes 4b. The voltage across one of these is fed to the inputs of a second wide band amplifier 34 in the probe unit. This also has a high imput impedance and good common mode rejection. The output signal of the amplifier 34 is representative of the instantaneous current between the electrodes 4b.

The output of the amplifier 34 is fed to a 90 degree lag circuit 36 so that the phase of the current representative signal is adjusted relative to the voltage representative signal. Since we are interested in the capacitance, and since this signal is proportional to the product of capacitance and frequency, the lag circuit 36 also introduces an amplitude response of $-20$ dB/decade. This enables the apparatus to operate at different frequencies to suit different cultures or conditions so that, as explained above, the $\beta$-dispersion is essentially complete but the $\alpha$-dispersion is substantially insignificant.

The voltage representative signal output of the amplifier 26, is also fed to the reference input of a phase sensitive detector 38. The signal input of the phase sensitive detector 38 is fed by the output of the lag circuit 36. The output of the phase sensitive detector 38 is representative of the amplitude of that component of the signal input which is in phase with the reference input. This thus represents the component of the current representative signal which lags the voltage representative signal by 90 degrees. Since the voltage between the electrodes 4a signal is constant, the output of the phase sensitive detector 38 is representative of the capacitance between the electrodes 4a. As the cell constant of the electrode arrangement is fixed by its size and geometry, the output of the phase sensitive detector is representative of the permittivity of the culture in the fermenter.

The output signal from the phase sensitive detector 38 is fed to an input of an amplifier 40 where it is summed with a second offset input adjusted to give a zero output signal when the fermenter contains only medium and no culture. The output of the amplifier 40 is representative of the change in capacitance, and thus permittivity, produced by any cells in the culture. As explained above, the signal thus represents biovolume: the proportion of the culture which is occupied by the cells.

It can also be useful to know the conductivity of the culture. A signal representative of the conductivity is derived in the present embodiment, by a second phase sensitive detector 42. The reference input for this detector is again the voltage representative signal output of the amplifier 26. The signal input of the detector 42 is the current representative signal output of the amplifier 34. In this case the detector thus produces an output signal which is representative of the amplitude of the component of the unadjusted current signal, which is in phase with the voltage representative signal at the reference input. Since, as before, the voltage between the electrodes 4a is fixed by the control loop, the output of the phase sensitive detector 42 represents the conductance between the electrodes 4a.

The biovolume and conductivity representative signals may be fed to respective meters as shown, and/or may be used directly in the control loop illustrated in FIG. 4.

In use the conductance signal is relatively large compared with the capacitance signal due to the small phase angle of the total vector admittance of the culture. In order to prevent distortion swamping the capacitance dependent signal, the oscillator should be as free from harmonics as possible and the amplifiers and lag circuits etc. should be very low distortion circuits and the phase sensitive detector 38 may also be used to further reduce residual harmonic responses.

In use the electrodes may become contaminated. Any biofilm or other adherent matter may cause the signals generated by the analyser to be unrepresentative of the bulk culture suspension. In order to clean them a relatively large current pulse is applied between them periodically by a cleaning pulse generator 44. Diodes provide isolation between this circuit and the RF signals. The cleaning pulses are of sufficient magnitude to effect electrolysis at the electrodes. During the cleaning pulses, the values of the output biovolume and conductivity signals, are maintained by track and hold circuits 46.

We claim:

1. Apparatus for determining biomass in a medium comprising a suspending fluid and cells, the apparatus comprising: mutually spaced electrodes for placing in the medium in electrical contact therewith; and means for generating a signal dependent on the capacitance between the electrodes, at a predetermined frequency or over a predetermined range of frequencies between 0.1 MHz and 10 MHz, said electrodes including a pair of voltage sensing electrodes between a pair of current electrodes, and the means for generating the capacitance dependent signal, comprising: means for applying an alternating voltage, at the predetermined frequency, between the current electrodes; means for providing a current signal indicative of the instantaneous current in the current electrode circuit; means for providing a voltage signal indicative of the instantaneous voltage between the voltage electrodes; and means for determining the ratio between the value of the voltage signal and the value of a quadrature component of the current signal, or vice versa, to provide the capaitance dependent signal.

2. Apparatus as claimed in claim 1, including means for controlling the amplitude of said alternating voltage, so as to maintain the amplitude of the voltage signal at a reference level.

3. Apparatus as claimed in claim 2, wherein the means for determining the ratio, comprises means for adjusting the current and/or voltage signal to produce a 90 degree phase lag of the current signal relative to the voltage signal, and a phase sensitive detector having a reference input responsive to the relatively adjusted voltage signal and a signal input responsive to the relatively adjusted current signal to generate the capacitance dependent signal representative of the in phase component of said relatively adjusted current signal.

4. Apparatus as claimed in any of claims 1 to 3, wherein the means for providing current signal and the means for providing the voltage signal each include respective high input impedence, high common mode rejection amplifiers.

5. Apparatus as claimed in claim 4, wherein the means for applying an alternating voltage, includes an isolating transformer.

6. Apparatus as claimed in claim 1, including means for applying relatively large alternating polarity cleaning pulses to the electrodes.

7. Apparatus for performing a fermentation utilising a culture comprising a suspending liquid and cells, the apparatus comprising: a fermenter for containing the culture, electrodes mutually spaced in the fermenter so as to be in contact with the culture in use, including a pair of voltage sensing electrodes between a pair of current electrodes, and means for generating a signal dependent on the capacitance between the electrodes, at a predetermined frequency, wherein the means for generating the capacitance dependent signal, comprises: means for applying an alternating voltage, at the predetermined frequency, between the current electrodes; means for providing a current signal indicative of the instantaneous current in the current electrode circuit; means for providing a voltage signal indicative of the instantaneous voltage between the voltage electrodes; and means for determining the ratio between the value of the voltage signal and the value of a quadrature component of the current signal, or vice versa, to provide the capacitance dependent signal.

8. Apparatus as claimed in claim 7, including means for controlling the amplitude of said alternating voltage, so as to maintain the amplitude of the voltage signal at a reference level.

9. Apparatus as claimed in claim 8, wherein the means for determining the ratio, comprises means for adjusting the current and/or voltage signal to produce a 90 degree phase lag of the current signal relative to the voltage signal, and a phase sensitive detector having a reference input responsive to the relatively adjusted voltage signal and a signal input responsive to the relatively adjusted current signal to generate the capacitance dependent signal representative of the in phase component of said relatively adjusted current signal.

10. Apparatus as claimed in any of claims 7 to 9, wherein the means for providing current signal and the means for providing the voltage signal each include respective high input impedance, high common mode rejection amplifiers.

11. Apparatus as claimed in claim 9, wherein the means for applying an alternating voltage, includes as isolating transformer.

12. Apparatus as claimed in claim 7, including means for applying relatively large alternating polarity cleaning pulses to the electrodes.

* * * * *